(12) United States Patent
Drewry et al.

(10) Patent No.: US 7,909,855 B2
(45) Date of Patent: Mar. 22, 2011

(54) ORTHOPEDIC IMPLANT ASSEMBLY

(75) Inventors: Troy D. Drewry, Memphis, TN (US); William B. Null, Olive Branch, MS (US); Marc T. Paul, Memphis, TN (US)

(73) Assignee: Warsaw Orthopedics, Inc., Warsaw, IN (US)

( * ) Notice: Subject to any disclaimer, the term of this patent is extended or adjusted under 35 U.S.C. 154(b) by 1191 days.

(21) Appl. No.: 11/581,915

(22) Filed: Oct. 17, 2006

(65) Prior Publication Data
US 2008/0177325 A1    Jul. 24, 2008

(51) Int. Cl.
*A61B 17/70* (2006.01)
(52) U.S. Cl. ........................................ 606/265; 606/266
(58) Field of Classification Search .................. 606/250, 606/251, 272, 265, 266
See application file for complete search history.

(56) References Cited

U.S. PATENT DOCUMENTS

| | | | |
|---|---|---|---|
| 6,875,211 B2 * | 4/2005 | Nichols et al. | 606/914 |
| 2005/0277927 A1 * | 12/2005 | Guenther et al. | 606/61 |

* cited by examiner

*Primary Examiner* — Eduardo C Robert
*Assistant Examiner* — Elana B Fisher

(57) ABSTRACT

Embodiments of an orthopedic implant assembly include an apparatus having a receiver member and a fixation member. The receiver member includes first and second branches which define a channel extending along a longitudinal axis. The channel is configured to receive an elongated member. Additionally, the fixation member can include a threaded portion configured to engage bone. The orthopedic implant system can further include a one-step locking mechanism operably connected with the receiver member, the locking mechanism being configured to lock an elongated member in the channel. The locking mechanism includes a first closure device operably connected with the first branch and a second closure device operably connected with the second branch. The first and second closure devices are configured to cooperate with each other along a lateral axis to lock an elongated member in the channel. In certain embodiments, the lateral axis does not intersect the longitudinal axis.

32 Claims, 6 Drawing Sheets

ORTHOPEDIC IMPLANT ASSEMBLY

The present disclosure broadly concerns spinal fixation systems useful for correction of spinal injuries or deformities. The present disclosure generally relates to mechanisms used to connect orthopedic implants with elongated members, such as spinal rods, for therapeutic or corrective purposes. More specifically, but not exclusively, the present disclosure contemplates an orthopedic assembly having a one-step locking mechanism capable of selectively locking an elongated member with respect to an orthopedic device.

In the realm of orthopedic surgery, it is well known to use implants to fix the position of bones. In this way, the healing of a broken bone can be promoted, and malformations or other injuries can be corrected. For example, in the field of spinal surgery, it is well known to place such implants into vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Implant and connection systems may include several pieces, which may be associated with only specific other pieces. Bone screws, hooks, clamps or other fixation devices can be connected or adjoined to a particular bone as a connection between the bone and the connection system, which can include a support and/or stabilizing member such as a spinal rod. In such a system, a series of two or more screws may be inserted into two or more vertebrae to be instrumented. A rod is then placed within or coupled to the screws, or is placed within a connecting device that links the rod and a screw, and the connections are tightened. In certain instances, screws or other such retaining members can be used to maintain the rod in a channel. In this way, a rigid supporting structure is fixed to the vertebrae, with the rod providing the support that promotes correction or healing of the vertebral malformation or injury by keeping the vertebrae in a particular position.

DESCRIPTION OF THE ILLUSTRATED EMBODIMENTS

Figure 1:
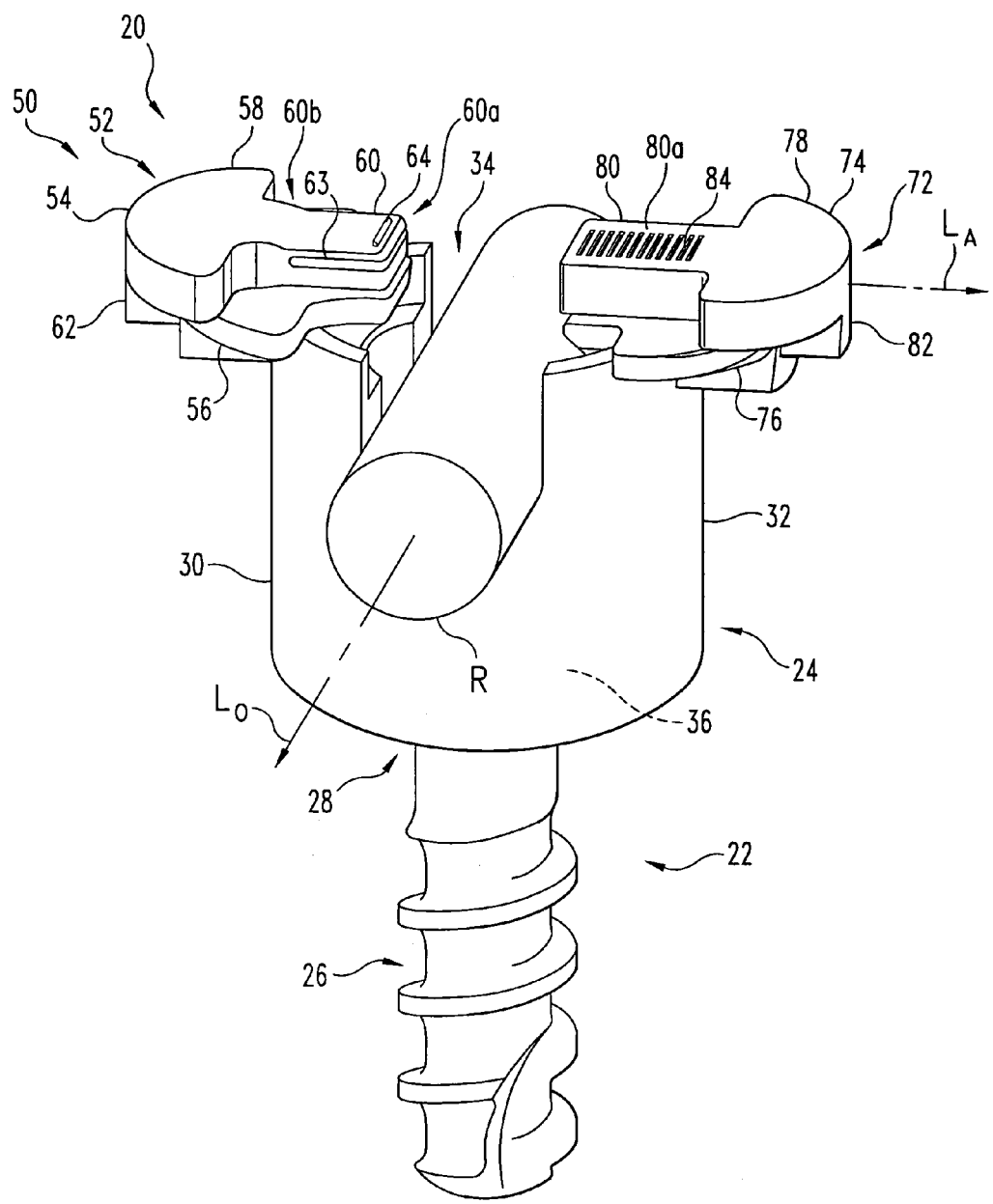
FIG. 1 is a perspective view of an embodiment of an orthopedic implant assembly.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring generally to FIGS. 1-4, there is shown an embodiment of an orthopedic implant assembly 20 having a fixation element such as a bone screw 22, a receiver member 24, and a locking mechanism 50. Assembly 20 is configured so that bone screw 22 or another fixation member can be connected with an elongated member, such as spinal rod R. Bone screw 22 includes a threaded bone engaging portion 26 and a head portion 28. Bone engaging portion 26 of bone screw 22 can be at least partially advanced into a bone structure or other tissue to secure the positioning of receiver member 24 and spinal rod R adjacent the underlying bone structure. Orthopedic implant assembly 20 can provide correction, support or other benefit to an orthopedic surgical site.

In the illustrated embodiment, bone engaging portion 26 of bone screw 22 is threaded to engage a bone structure, such as a vertebral body, and solidly anchor bone screw 22 to the bone structure. Bone engaging portion 26 can include coarse threads readily adapted for solid fixation within the cancellous bone of a vertebral body and can terminate in a tapered tip to assist in the gradual engagement and advancement of the threads into the vertebral body. In alternative embodiments, it should be appreciated that the bone engaging portion can have a variety of configurations and/or can be hooks, clamps, bolts or other such appropriate fixation members for connecting to tissue such as bone.

The illustrated embodiment of receiver member 24 includes two branches 30 and 32 defining a U-shaped channel 34 for accommodating an elongated member, such as spinal rod R. In that embodiment, channel 34 extends along a longitudinal axis Lo substantially along or parallel to which an elongated member can lie. In the illustrated embodiment, branches 30 and 32 are shown extending generally upward or away from bone screw 22 and the remainder of receiver member 24, but in other embodiments, branches 30 and 32 could be otherwise oriented, such as forming a side opening channel as an example. Additionally, branches 30 and 32 are shown generally parallel to each other and somewhat planar, and in other embodiments could be non-parallel with each other and/or curved.

Receiver member 24, in that embodiment, also defines a lower opening portion 36, in communication with channel 34, and an aperture 29 in communication with lower opening portion 36. Aperture 29 receives a portion of bone screw 22, to thereby engage bone screw 22 with receiver member 24. In the illustrated embodiment, head portion 28 is shaped and sized to fit within at least lower opening area 36 to engage bone screw 22 with receiver member 24. Accordingly, lower opening portion 36 can include a width that is larger than the width or diameter of head portion 28 of bone screw 22. Aperture 29 has a width smaller than head portion 28, so that head 28 can rest on the edges of aperture 29.

Orthopedic implant assembly 20 further includes locking mechanism 50, which in this embodiment is able to be locked in one step. Locking mechanism 50 includes a first inserting closure device 52 and a second receiving closure device 72. Closure devices 52 and 72 can be operably connected with branches 30 and 32, as describe and illustrated herein. Additionally, closure devices 52 and 72 can be configured to cooperate along a lateral axis $L_A$ to at least partially close an entrance into channel 34 and selectively lock spinal rod R in channel 34. In certain embodiments, lateral axis LA does not intersect longitudinal axis $L_O$.

Closure device 52 includes a clip member 54 and a spacer member 56. Clip member 54 generally includes a handle portion 58, an extension portion 60 and a tenon portion 62. Extension portion 60 has an end 60a distal from handle portion 58 and an end 60b connected to handle portion 58, and includes an open slot 63 and a tab, such as clip projection 64. Projection 64 is generally positioned near end 60a. In certain embodiments, slot 63 can extend the width of extension portion 60 and extend from end 60a toward end 60b. Slot 63 allows for compression of extension portion 60 to assist in the insertion of portion 60 into hollow portion 80.

Closure device 72 includes a clip member 74 and a spacer member 76. Clip member 74 generally includes a handle portion 78, a hollow portion 80 and a tenon portion 82. Hollow portion 80 is configured to at least partially receive extension portion 60. Accordingly, extension portion 60 has a slightly smaller cross-sectional dimension than hollow portion 80. Hollow portion 80 has a top surface 80a and includes one or more grooves or slots 84 in top surface 80a configured to receive clip projection 64 to selectively lock closure devices 52 and 72 together.

Figure 2:
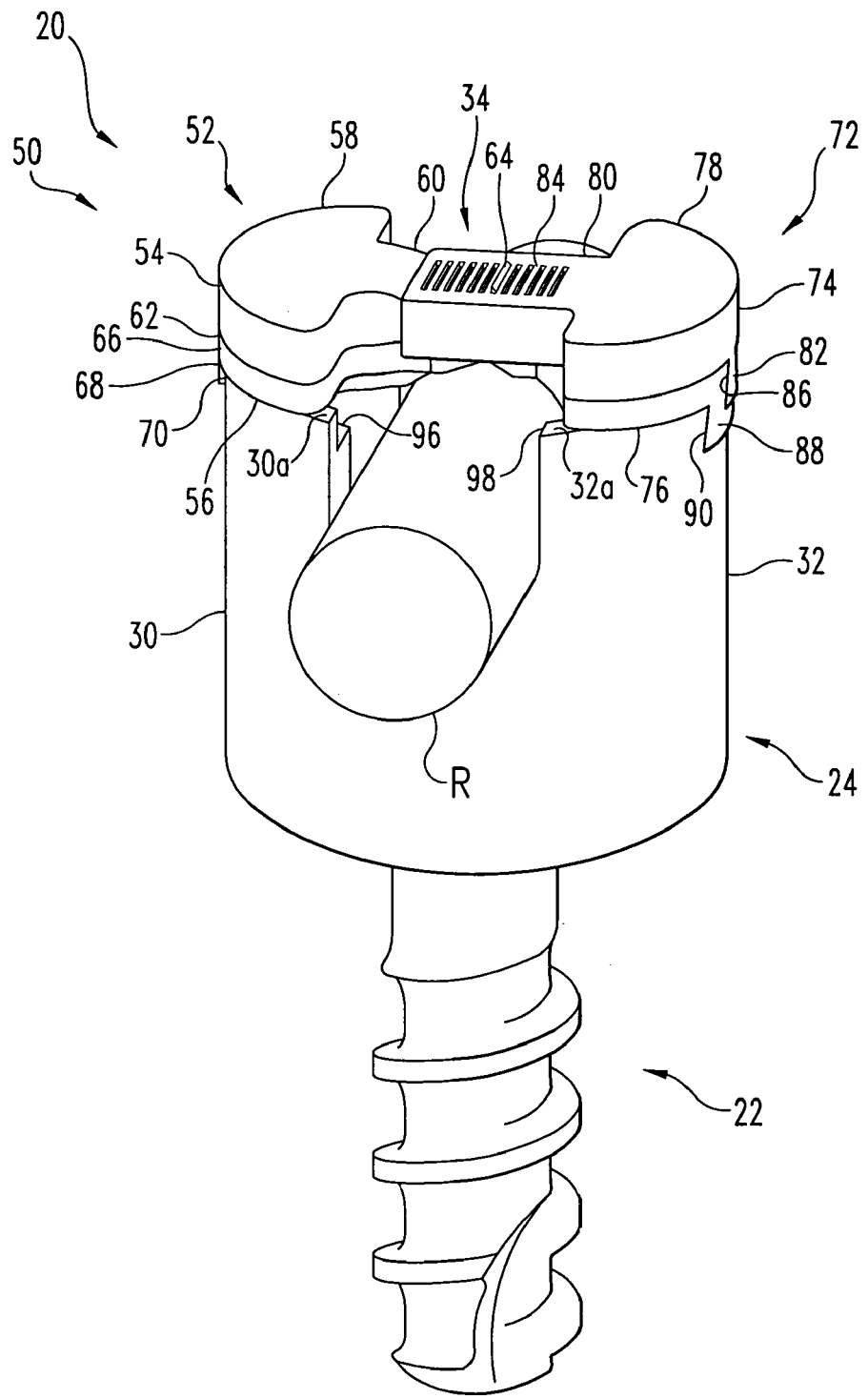
FIG. 2 is another perspective view of the embodiment shown in FIG. 1.

FIG. 2 illustrates orthopedic implant assembly 20 in a locked position, such that spinal rod R is maintained or is substantially locked within channel 34. In the illustrated embodiment, spacer members 56 and 76 define channels or grooves, such as mortises 66 and 86, respectively, configured to engage tenon portions 62 and 82. In such embodiments, clip members 54 and 74 are slidable within spacer members 56 and 76, respectively. Additionally, in the illustrated embodiment, spacer members 56 and 76 include projections, such as tenon portions 68 and 88. To engage tenon portions 68 and 88, branches 30 and 32 having top surfaces 30a and 32a, respectively, can define channels or grooves, such as mortises 70 and 90, respectively. Mortises 70 and 90 are configured to slidably engage tenon portions 68 and 88 of spacer members 56 and 76.

The mortise and tenon connections engaging clip members 54 and 74 to spacer members 56 and 76, and engaging spacer members 56 and 76 to branches 30 and 32 of receiver member 24 can be configured as dovetail joints having wedged shaped mortises and tenon portions. In the illustrated embodiment, mortises 66, 86, 70 and 90 and corresponding tenon portions 62, 82, 68 and 88 include generally trapezoidal shapes with outwardly sloping side surfaces, sloping outward in a direction from clip members 54 and 74 toward branches 30 and 32 of receiver member 24. It will be understood that other shapes of such mortises and/or tenon portions could be used. In certain embodiments, tenon portions 62, 82, 68 and 88 include sloping side surfaces which are generally adjacent or abut the sloping side surfaces of mortises 66, 86, 70 and 90, respectively, with the angle of the side surfaces of the tenon portions being about the same as the angle of the side surfaces of the corresponding mortises.

In certain embodiments, tenon portions 62, 82, 68 and 88 can include stop extensions at distal ends thereof to prevent slideable movement of tenon portions 62, 82, 68 and 88 in corresponding mortises 66, 86, 70 and 90 beyond certain positions, e.g. to hinder or prevent removal of one of such mortises from a corresponding tenon portion, or to hinder or prevent removal of one of such tenon portions from a branch of receiver member 24. Alternative configurations of mortises 66, 86, 70 and 90 and tenon portions 62, 82, 68 and 88 are contemplated, such as generally inverted T-shaped configurations. Additionally, it should be appreciated that clip members 54 and 74 and spacer members 56 and 76 can be slidably engaged to each other and to receiver member 24 in other appropriate members as would occur to one skilled in the art. As in the illustrated embodiment, branches 30 and 32 can define inner grooves or shelves 96 and 98 so that spacer members 56 and 76 can translate or slide along shelves 96 and 98, respectively, near top surfaces 30a and 32a of branches 30 and 32.

Figure 3:
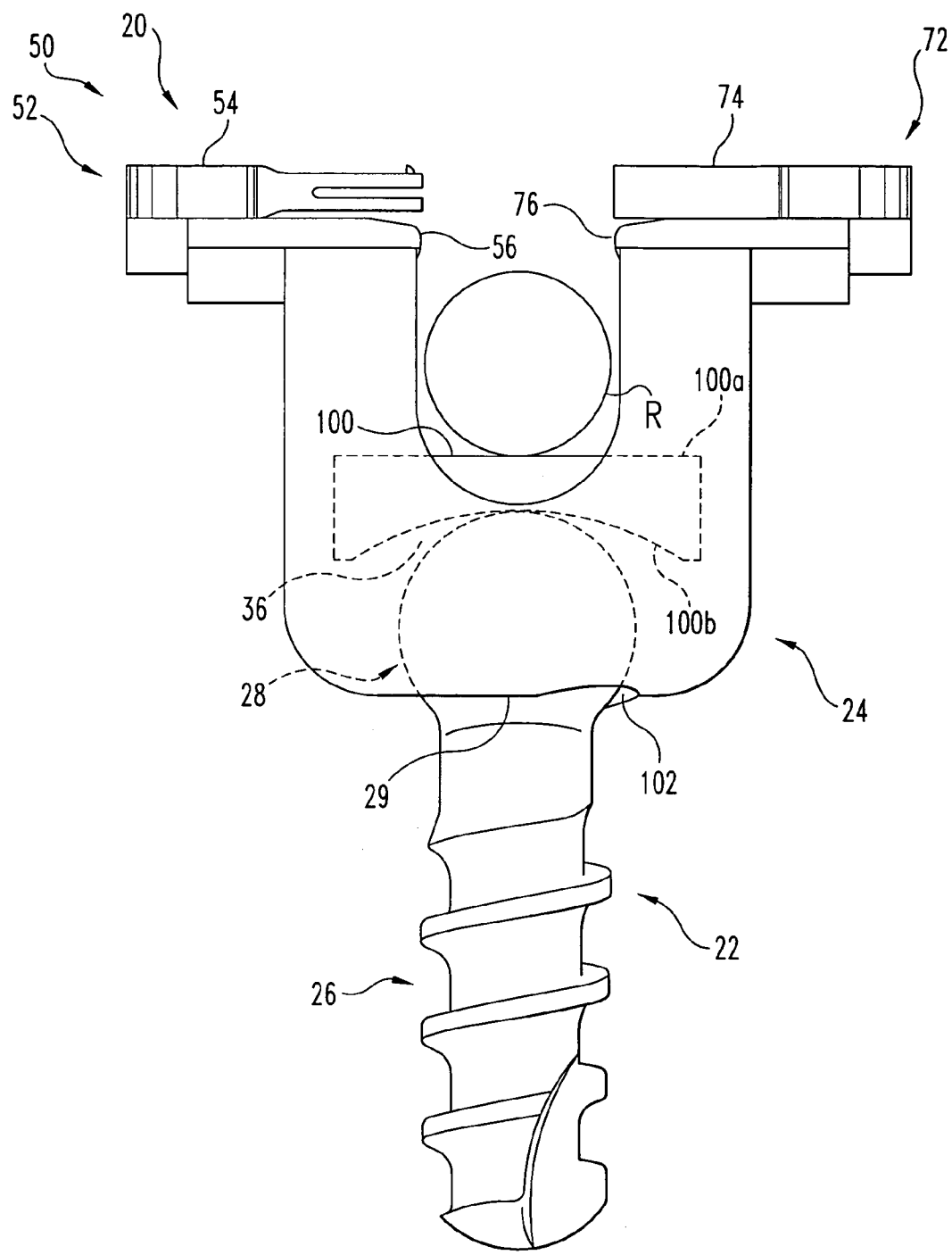
FIG. 3 is a top view of the embodiment shown in FIG. 1.
Figure 4:
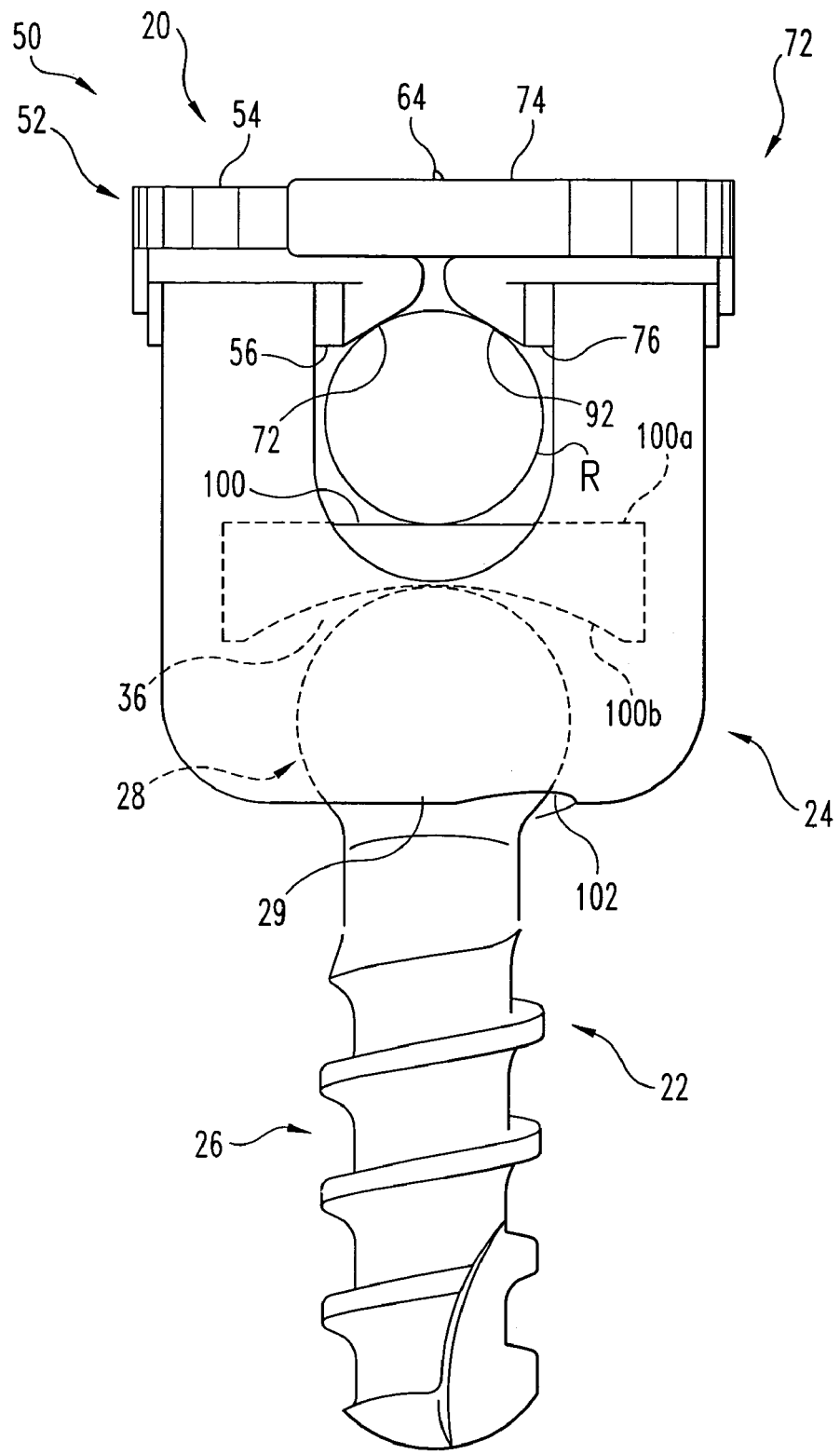
FIG. 4 is another top view of the embodiment shown in of FIG. 1.

FIGS. 3 and 4 correspond to FIGS. 1 and 2, respectively and are top views of orthopedic implant assembly 20 in the unlocked and locked positions. Fixation member 22 could be a bone screw identical or similar to those shown in commonly-owned U.S. Pat. Nos. 6,280,442; 5,797,911; or 5,005,562, all of which are incorporated herein by reference in their entireties. As an illustrated embodiment, orthopedic implant assembly 20 is a multi-axial screw assembly, including a crown member 100 having an upper surface 100a and a lower surface 100b. Accordingly, in certain embodiments, bone screw 22 can occupy various angular positions with respect to spinal rod R in channel 34. In the illustrated embodiment, crown member 100 is in the shape of a substantially circular disc. In certain embodiments, crown member 100 can be sized and shaped to fit within at least lower opening portion 36, so that crown member 100 is slidably and rotatably movable within lower opening portion 36. Additionally, in certain embodiments, crown member 100 is configured such that crown member 100 cannot move into channel 34. In alternative embodiments, orthopedic implant assembly 20 can be a single connecting device, such as a fixed axis bone screw or a pivoting bone screw.

Head portion 28 forms at least part of a sphere in the illustrated embodiment, though alternative curvate and other configurations may be employed. In the illustrated embodiment, lower surface 100b of crown member 100 includes a generally spherical shape to fittingly contact the generally spherical surface of head portion 28 of bone screw 22, allowing for relative movement of head portion 28 within lower opening portion 36 of receiver member 24. The diameter of surface 100b may be substantially the same as the diameter of head portion 28 in some embodiments. However, it should be appreciated that lower surface 100b can have one or more other shapes, such as a beveled or conical shape. Additionally, lower surface 100b can be provided with a friction-enhancing surface configuration (e.g. roughening or knurling) for cooperation with head portion 28 of bone screw 22. Similarly, in certain embodiments, head portion 28 can include a series of ridges for improving engagement with lower surface 100b of crown member 100. In other embodiments, head portion 28 may have alternative friction-increasing surface configurations, such as roughening or knurling.

In certain embodiments, head portion 28 of bone screw 22 can include a drive-tool-engaging structure or configuration associated therewith, such as an internal hexagonal receiving portion configured to cooperate with a bone screw-driving tool or instrument. Accordingly, it is contemplated that crown member 100 can include a hole to allow for contact with head portion 28 of bone screw 22 through receiver member 24.

As illustrated in FIG. 4, spacer members 56 and 76 can include convex surfaces 72 and 92, respectively, to contact the curved outer surface of spinal rod R and urge spinal rod R in channel 34, pushing spinal rod R down on crown member 100. Crown member 100 then exerts a force on bone screw 22 to hold or lock bone screw 22 in a desired angular position relative to receiver member 24. In certain embodiments, receiver member 24 can include a cut-away portion 102, in communication with aperture 29, to allow for additional angular movement of bone screw 22 relative to receiver member 24.

Figure 5:
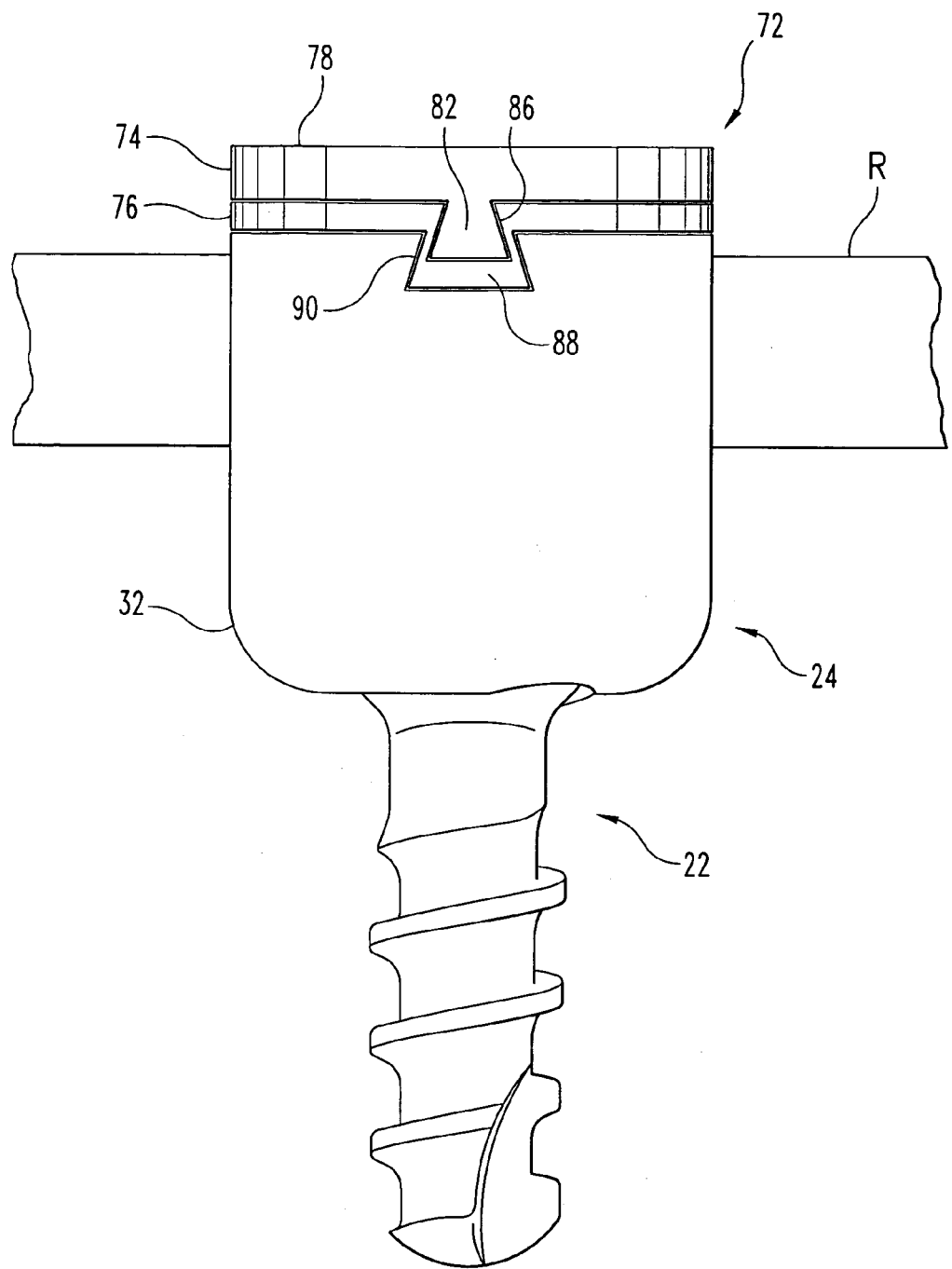
FIG. 5 is a side view of the embodiment shown in FIG. 1.

Referring to FIG. 5, there is illustrated a side view of orthopedic implant assembly 20. FIG. 5 illustrates the mortise and tenon portions of orthopedic implant assembly 20 allowing slidable engagement between clip members 54 and 74 to spacer members 56 and 76, and the slidable engagement of spacer members 56 and 76 to branches 30 and 32 of receiver member 24. The wedge-shaped mortise and tenon joints or dovetail connections created by the outwardly sloping surfaces of the mortises 66, 86, 70 and 90 and tenon portions 62, 82, 68 and 88 prevent disengagement of the components of orthopedic implant assembly 20. As an example, the wedge-shaped connections prevent clip members 54 and 74 from disengaging from spacer members 56 and 76.

Figure 6:
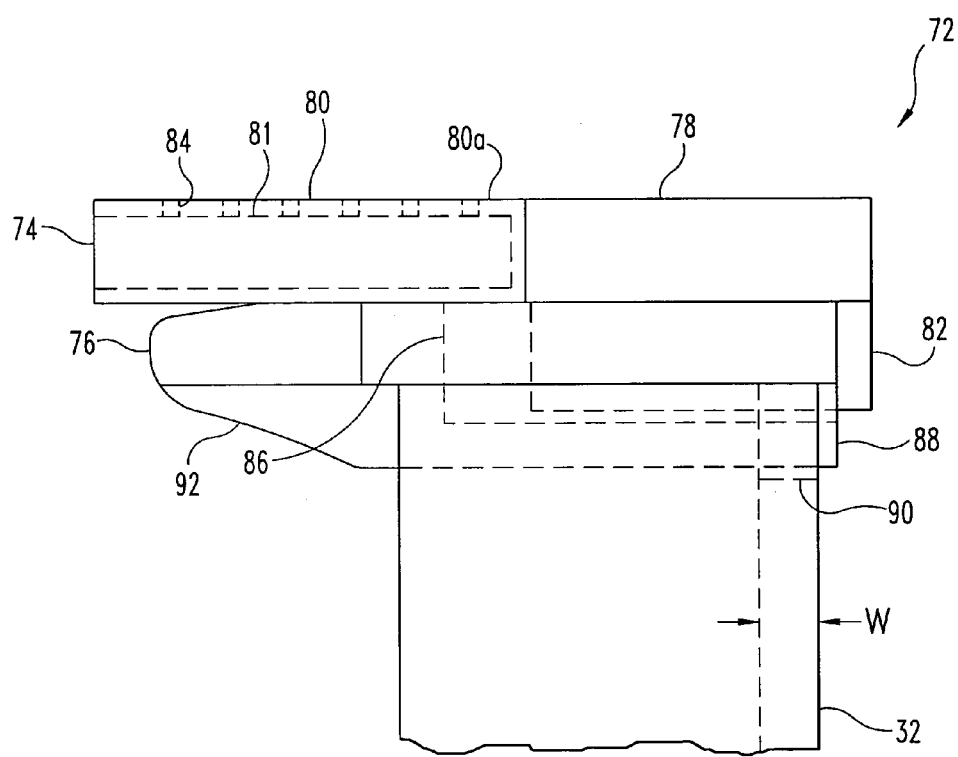
FIG. 6 is a top view of a portion of the embodiment shown in FIG. 1.

FIG. 6 illustrates a top view of components of closure device 72 and a portion of branch 32 of receiver member 24. As illustrated, clip member 74 defines a cavity 81 configured to receive extension portion 60 of clip member 54. Additionally, tenon portion 82 is configured to translate or slide within mortise 86 and tenon portion 88 is configured to translate or slide within mortise 90 of branch 32. These connections permit relative movement of clip member 74 and spacer member 76 relative to branch 32 of receiver member 24 to lock and unlock spinal rod R in channel 34. It should be appreciated that closure device 52 is similar in configuration and operation to closure device 72 regarding the mortise and tenon connections, and thus closure device 52 has not been illustrated for the sake of brevity.

Referring generally to FIGS. 1-6, the operation and use of orthopedic implant assembly 20 will be described with reference to a surgical procedure involving a section of spine. It will be appreciated that other uses of instrument 20 in other surgical procedures can be made.

To treat the condition or injury of the patient, the surgeon obtains access to the surgical site in any appropriate manner, e.g. through incision and retraction of tissues. It is contemplated that orthopedic implant assembly 20 discussed herein can be used in minimally-invasive surgical techniques where the disc space is accessed through a micro-incision, a sleeve, or one or more retractors that provide a protected passageway to the disc space. Orthopedic implant assembly 20 also has application in open surgical techniques where skin and tissue are incised and retracted to expose the surgical site.

Once access to the surgical site has been obtained, e.g. via an opening such as a midline incision above the affected area, with tissue being resected, or by other surgical procedure, the surgeon may connect one or more implants, such as orthopedic implant assembly 20 discussed herein, to adjacent or nearby vertebrae that require compression or distraction in order to relieve or improve their condition. For example, pilot holes in vertebrae may be made, and fixation elements, such as bone screw 22, may be inserted into or otherwise connected to two or more vertebrae. Bone engaging portion 26 of bone screw 22 can be threaded into the vertebrae to a desired depth and/or desired orientation relative to receiver member 24. In many instances of spinal surgery, a surgeon will orient receiver member 24 so that channel 34 is substantially parallel to a portion of the spine.

Spinal rod R can be placed in channel 34 so that spinal rod R contacts upper surface 100a of crown member 100. In the illustrated embodiment, orthopedic implant assembly 20 is a multi-axial bone screw assembly and accordingly bone screw 22 can be positioned at any one of a plurality of angular positions relative to receiver member 24 and spinal rod R. Crown member 100 remains slideably positioned in lower opening portion 36 of receiving member 24, and bone screw 22 remains multi-axially moveable with respect to crown member 100 and receiver member 24. Spinal rod R and bone screw 22 can be adjusted relative to each other or the adjacent vertebrae, as desired. Once any such adjustments are made, spinal rod R and bone screw 22 can be locked in the desired positions.

Orthopedic implant assembly 20 allows for spinal rod R to be locked in channel 34 via one-step locking mechanism 50. The locking of spinal rod R into channel 34 includes clip members 54 and 74 being urged toward each other. Mortises 66, 86, 70 and 90 and tenon portions 62, 82, 68 and 88 allow for clip members 54 and 74 and spacer members 56 and 76 to slide or translate relative to branches 30 and 32, respectively. More specifically, extension portion 60 can be received in cavity 81 of hollow portion 80, with slot 63 allowing for compression of extension portion 60 to ease the insertion of extension portion 60 in hollow portion 80. Extension portion 60 is inserted to a desired position whereby clip projection 64 is received in a desired slot 84.

As clip members 54 and 74 are clipped together, convex surfaces 72 and 92 of spacer members 56 and 76 contact spinal rod R and exert a force on spinal rod R to urge spinal rod R downward against upper surface 100a crown member 100. It will be seen that rods of various diameters can be used with an embodiment of an anchor having clip members such as members 54 and 74, particularly where spacer members 56 and 76 are made of resilient or compressible material. Relatively larger diameter rods can compress or deform to a relatively large degree or contact a greater surface area of spacer members 56 and 76, while relatively smaller diameter rods may contact or compress less of spacer members 56 and 76. Urging spinal rod R against crown member 100 causes crown member 100 to exert a force on head portion 28 of bone screw 22 and push down onto head portion 28. Head portion 28 is thereby clamped between receiver member 24 and crown member 100. In this way, bone screw 22 is locked at the desired angular position with respect to spinal rod R and the remainder of assembly 20.

To unlock orthopedic implant assembly 20, a force is exerted down onto extension portion 60 to disengage clip extension 64 from a corresponding groove or slot 84. Thereafter, clip members 54 and 74 can be moved away from each other and out of engagement. Thereafter, spinal rod R can be removed from channel 34 and/or bone screw 22 can be repositioned to a desired angular position relative to receiver member 24. Revision of an implanted support is thus made much easier than having to remove screws or nuts that lock rods to fixed implants.

It should be appreciated that locking mechanism 50 can be used with any other orthopedic implant having a rod-receiving channel, such as U-shaped channel 34, to lock an elongated member in the particular channel. For example, locking mechanism 50 can be used with a bone plate, clamp or connector having a channel configured to receive a rod or other elongated member. In embodiments of plates or hooks having channel(s) like channel 34, for example, rod R can be pre-loaded into such a channel at a desired position either before or after placement of the implant adjacent or around bone tissue or structure. Additionally, rod R can be pre-bent to conform to a particular spinal or other tissue curvature or as a particular correction, support or therapy requirement may dictate, or the elongated member can be bent in situ.

The components of orthopedic implant assembly 20 can be composed of biocompatible materials that are also compatible with particular elongated members or other implants with which orthopedic implant assembly 20 will be used. Thus, orthopedic implant assembly 20 may be made of titanium, nickel, alloys of titanium and nickel, stainless steel, certain sturdy plastic materials, or other sturdy materials. The materials chosen for orthopedic implant assembly 20 should be the same as those of the rods with which orthopedic implant assembly 20 is used, or at least of a material that will not cause discomfort or an adverse reaction when used with the rods. It will be appreciated that materials other than those described above could also be used.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus, comprising:
an orthopedic implant device having a receiver member and a fixation member;
wherein said receiver member includes first and second branches, each having a top surface, wherein said branches define a channel extending along a longitudinal axis, said channel being configured to receive an elongated member, wherein said fixation member includes a threaded portion configured to engage bone;
a locking mechanism operably connected with said receiver member and configured to substantially close at least part of said channel and lock an elongated member in said channel;
wherein said locking mechanism includes a first closure device operably connected with said first branch and a second closure device operably connected with said second branch, wherein said first closure device is configured to slide together with said second closure device along a lateral axis to lock an elongated member in said channel; and
wherein said first and second closure devices define a tapered contact surface that tapers along said lateral axis with said tapered contact surface positioned in contact with an outer surface of said elongated member as said first and second closure devices are slid together along said lateral axis to thereby exert a downward force onto said elongated member and lock said elongated member in said channel.

2. The apparatus of claim 1, wherein said first and second closure devices are operably connected with said first and second branches proximal said corresponding top surfaces of said branches.

3. The apparatus of claim 1, wherein said fixation member is positionable at a plurality of angular positions relative to said receiver member.

4. The apparatus of claim 3, wherein said fixation member includes a head portion configured to be moveably disposed in said receiver member.

5. The apparatus of claim 1, wherein said orthopedic implant device is a fixed-axis bone screw.

6. The apparatus of claim 1, wherein said first closure device includes a clip member having a hollow portion and said second closure device includes a clip member having an extension portion, wherein said extension portion is configured to be at least partially received in said hollow portion.

7. The apparatus of claim 6, wherein said extension portion includes a clipping projection, wherein said hollow portion includes a top surface and defines at least one slot in said top surface configured to receive said clipping projection to selectively lock said first closure device to said second closure device.

8. The apparatus of claim 1, wherein said tapered contact surface of said first and second closure devices defines a convex surface section positioned in contact with a curved outer surface of said elongated member to thereby exert said downward force onto said elongated member and lock said elongated member in said channel.

9. An apparatus, comprising:
an orthopedic implant device having a receiver portion and a fixation portion;
wherein said receiver member includes first and second branches, each having a top surface, wherein said branches define a channel extending along a longitudinal axis, said channel being configured to receive an elongated member, wherein said fixation member includes a threaded portion configured to engage bone;
a locking mechanism operably connected with said receiver member and configured to substantially close at least part of said channel and lock an elongated member in said channel;
wherein said locking mechanism includes a first closure device operably connected with said first branch and a second closure device operably connected with said second branch, wherein said first closure device is configured to slide together with said second closure device along a lateral axis to lock an elongated member in said channel; and
wherein said first and second closure devices each include a clip member and a spacer member, wherein each of said clip members is configured to slideably engage said corresponding spacer member, wherein each of said spacer members is configured to slideably engage said corresponding branch.

10. The apparatus of claim 9, wherein each of said clip members is configured to slideably engage said corresponding spacer member via a dovetail connection; and
wherein each of said spacer members is configured to slideably engage said corresponding branch via a dovetail connection.

11. A multi-axial bone-engaging anchor assembly for engagement to an elongated member, comprising:
a receiver member having first and second side extensions defining a channel, wherein said receiver member defines a lower opening portion having a respective minimum width, wherein said channel is configured to receive the elongated member and is in communication with said lower opening portion, said side extensions each having a top surface;
a bone-engaging anchor having a lower threaded portion configured to engage bone and a head having a width, said width of said head being smaller than said minimum width of said lower opening portion, said head being movably disposed in said lower opening portion; and
a closure mechanism operably connected with said receiver member and configured to selectively to lock the elongated member in said channel;
wherein said closure mechanism includes a first closure device operably engaged with said first side extension proximal said top surface of said first side extension and a second closure device operably engaged with said second side extension proximal said top surface of said second side extension, wherein said first closure device is configured to cooperate with and engage said second closure device along a lateral axis in a direction generally perpendicular to said channel to lock the elongated member in said channel; and
wherein said first and second closure devices define a tapered contact surface that tapers along said lateral axis with said tapered contact surface positioned in contact with an outer surface of said elongated member as said first and second closure devices are engaged along said lateral axis to thereby exert a downward force onto said elongated member and lock said elongated member in said channel.

12. The assembly of claim 11, comprising a crown member movably disposed in said lower opening portion, said crown member including an upper surface and a lower surface, wherein said head is moveably disposed in said lower opening portion adjacent to said lower surface of said crown member.

13. The assembly of claim 12, wherein said head of said bone-engaging anchor is at least partially spherical and said lower surface of said crown member is at least partially spherical.

14. The assembly of claim 11, wherein said bone-engaging anchor is a bone screw and the elongated member is a spinal rod.

15. The assembly of claim 11, wherein said first closure device includes a clip member having a hollow portion and said second closure device includes a clip member having an insertion portion, wherein said insertion portion is configured to be at least partially received in said hollow portion.

16. The assembly of claim 15, wherein said insertion portion includes a clipping projection, wherein said hollow portion includes a top surface and defines at least one receiving slot in said top surface configured to receive said clipping projection to selectively lock said first closure device to said second closure device.

17. The assembly of claim 16, wherein said insertion portion includes a distal end and a proximal end, said proximal end being nearer to said first closure device than said distal end, wherein said insertion portion has a width and includes a slot extending said width of said extension portion from said proximal end toward said distal end.

18. The assembly of claim 11, wherein said tapered contact surface of said first and second closure devices defines a convex surface section positioned in contact with a curved outer surface of said elongated member to thereby exert said downward force onto said elongated member and lock said elongated member in said channel.

19. A multi-axial bone-engaging anchor assembly for engagement to an elongated member, comprising:
 a receiver member having first and second side extensions defining a channel, wherein said receiver member defines a lower opening portion having a respective minimum width, wherein said channel is configured to receive the elongated member and is in communication with said lower opening portion, said side extensions each having a top surface;
 a bone-engaging anchor having a lower threaded portion configured to engage bone and a head having a width, said width of said head being smaller than said minimum width of said lower opening portion, said head being movably disposed in said lower opening portion; and
 a closure mechanism operably connected with said receiver member and configured to selectively to lock the elongated member in said channel;
 wherein said closure mechanism includes a first closure device operably engaged with said first side extension proximal said top surface of said first side extension and a second closure device operably engaged with said second side extension proximal said top surface of said second side extension, wherein said first closure device is configured to cooperate with said second closure device in a direction generally perpendicular to said channel to lock the elongated member in said channel; and
 wherein said first and second closure devices each include a clip member and a spacer member, wherein each of said clip members is configured to slideably engage said corresponding spacer member, wherein each of said spacer members is configured to slideably engage said corresponding side extension.

20. The assembly of claim 19, wherein each of said clip members includes a tenon portion and each of said spacer members defines a corresponding mortise configured to engage said tenon portions of said clip members, wherein each of said spacer members includes a tenon portion and each of said top surfaces of said side extensions defines a corresponding mortise configured to engage said tenon portions of said spacer members.

21. A multi-axial bone-engaging anchor assembly for engagement to an elongated member, comprising:
 a receiver member having first and second side extensions defining a channel, wherein said receiver member defines a lower opening portion having a respective minimum width, wherein said channel is configured to receive the elongated member and is in communication with said lower opening portion, said side extensions each having a top surface;
 a bone-engaging anchor having a lower threaded portion configured to engage bone and a head having a width, said width of said head being smaller than said minimum width of said lower opening portion, said head being movably disposed in said lower opening portion; and
 a closure mechanism operably connected with said receiver member and configured to selectively to lock the elongated member in said channel;
 wherein said closure mechanism includes a first closure device operably engaged with said first side extension proximal said top surface of said first side extension and a second closure device operably engaged with said second side extension proximal said top surface of said second side extension, wherein said first closure device is configured to cooperate with said second closure device in a direction generally perpendicular to said channel to lock the elongated member in said channel; and
 wherein the elongated member includes a curved outer surface, wherein said first and second closure devices each include a spacer member having a convex surface section configured to fittingly contact the curved outer surface of the elongated member.

22. An apparatus, comprising:
 a fixation element having a threaded bone engaging portion and a head portion;
 a receiver member defining a channel extending along a longitudinal axis and configured to receive an elongated member, wherein said receiver member engages said fixation element, said receiver member including first and second branches defining said channel, each of said branches having atop surface;
 a clipping mechanism operably connected with said receiver member configured to selectively lock the elongated member in said channel;
 wherein said clipping mechanism includes a first clipping assembly including a clip member having a hollow portion, said first clipping assembly being operably engaged with said first branch proximal said top surface of said first branch, wherein said clipping mechanism further includes a second clipping assembly including a clip member having an extension portion, said second clipping assembly being operably engaged with said second branch proximal said top surface of said second branch, wherein said extension portion and said hollow portion are configured to clip together along a lateral axis arranged generally perpendicular to said longitudinal axis of said channel, with said extension portion configured to be at least partially received in said hollow portion; and wherein said first and second clipping assemblies define a tapered contact surface that tapers along said lateral axis with said tapered contact surface positioned in contact with an outer surface of said elongated member as said first and second clipping assemblies are clipped together along said lateral axis to thereby exert a downward force onto said elongated member and lock said elongated member in said channel.

23. The apparatus of claim 22, wherein said first and second clipping assemblies translates relative to one another along said lateral axis.

24. The apparatus of claim 23, wherein said lateral axis does not intersect said longitudinal axis.

25. The apparatus of claim 22, wherein said extension portion includes a distal end and a proximal end proximal said channel, wherein said extension portion includes a tab proximal said proximal end, wherein said hollow portion includes an upper surface and further defines at least one slot in said upper surface configured for receipt of said tab.

26. The apparatus of claim 25, wherein said extension portion includes a width and defines a slot extending said width of said extension portion from said proximal end toward said distal end.

27. The apparatus of claim 22, wherein said tapered contact surface of said first and second clipping assemblies defines a convex surface section positioned in contact with a curved outer surface of said elongated member to thereby exert said downward force onto said elongated member and lock said elongated member in said channel.

28. An apparatus, comprising:
a fixation element having a threaded bone engaging portion and a head portion;
a receiver member defining a channel extending along a longitudinal axis and configured to receive an elongated member, wherein said receiver member engages said fixation element, said receiver member including first and second branches defining said channel, each of said branches having a top surface;
a clipping mechanism operably connected with said receiver member configured to selectively lock the elongated member in said channel;
wherein said clipping mechanism includes a first clipping assembly including a clip member having a hollow portion, said first clipping assembly being operably engaged with said first branch proximal said top surface of said first branch, wherein said clipping mechanism further includes a second clipping assembly including a clip member having an extension portion, said second clipping assembly being operably engaged with said second branch proximal said top surface of said second branch, wherein said extension portion and said hollow portion are configured to clip together, with said extension portion configured to be at least partially received in said hollow portion; and
wherein each of said first and second clipping assemblies includes a spacer member positionable between said corresponding branch of said receiver member and said corresponding clip member, each of said spacer members defining a mortise, wherein each of said clip members includes a lower tenon portion configured to slideably engage said corresponding mortise of said corresponding spacer member.

29. The apparatus of claim 28, wherein each of said tenon portions and said mortises includes outwardly-sloped side surfaces forming a generally wedge-shaped cross-section, said side surfaces sloping outward in a direction from said corresponding clip member toward said corresponding branch of said receiver member.

30. An apparatus, comprising:
a fixation element having a threaded bone engaging portion and a head portion;
a receiver member defining a channel extending along a longitudinal axis and configured to receive an elongated member, wherein said receiver member engages said fixation element, said receiver member including first and second branches defining said channel, each of said branches having a top surface;
a clipping mechanism operably connected with said receiver member configured to selectively lock the elongated member in said channel;
wherein said clipping mechanism includes a first clipping assembly including a clip member having a hollow portion, said first clipping assembly being operably engaged with said first branch proximal said top surface of said first branch, wherein said clipping mechanism further includes a second clipping assembly including a clip member having an extension portion, said second clipping assembly being operably engaged with said second branch proximal said top surface of said second branch, wherein said extension portion and said hollow portion are configured to clip together, with said extension portion configured to be at least partially received in said hollow portion; and
wherein each of said top surfaces of said first and second branches defines a mortise, wherein each of said first and second branches includes a tenon portion configured to slideably engage said corresponding mortise defined in said corresponding top surface.

31. The apparatus of claim 30, wherein each of said tenon portions and said mortises includes outwardly-sloped side surfaces forming a generally wedge-shaped cross-section, said side surfaces sloping outward in a direction from said corresponding clip member toward said corresponding branch of said receiver member.

32. An apparatus, comprising:
a fixation element having a threaded bone engaging portion and a head portion;
a receiver member defining a channel extending along a longitudinal axis and configured to receive an elongated member, wherein said receiver member engages said fixation element, said receiver member including first and second branches defining said channel, each of said branches having a top surface;
a clipping mechanism operably connected with said receiver member configured to selectively lock the elongated member in said channel;
wherein said clipping mechanism includes a first clipping assembly including a clip member having a hollow portion, said first clipping assembly being operably engaged with said first branch proximal said top surface of said first branch, wherein said clipping mechanism further includes a second clipping assembly including a clip member having an extension portion, said second clipping assembly being operably engaged with said second branch proximal said top surface of said second branch, wherein said extension portion and said hollow portion are configured to clip together, with said extension portion configured to be at least partially received in said hollow portion; and
wherein the elongated member includes a curved outer surface, wherein each of said first and second clipping assemblies includes a spacer member having a convex surface segment configured to contact the curved outer surface of the elongated member and urge the elongated member in said channel.

* * * * *